(12) United States Patent
Eisenberg

(10) Patent No.: US 7,354,151 B2
(45) Date of Patent: Apr. 8, 2008

(54) RING LASER PHOTOCOAGULATION

(76) Inventor: Elliot S. Eisenberg, 1215 Greenwich, # 4A, San Francisco, CA (US) 94109

( * ) Notice: Subject to any disclaimer, the term of this patent is extended or adjusted under 35 U.S.C. 154(b) by 393 days.

(21) Appl. No.: 11/024,308

(22) Filed: Dec. 28, 2004

(65) Prior Publication Data

US 2005/0174538 A1  Aug. 11, 2005

Related U.S. Application Data

(60) Provisional application No. 60/540,810, filed on Jan. 30, 2004.

(51) Int. Cl.
*A61B 3/00* (2006.01)
(52) U.S. Cl. ............. 351/200; 351/205; 351/219; 351/246; 351/220
(58) Field of Classification Search ......... 351/200–247
See application file for complete search history.

(56) References Cited

U.S. PATENT DOCUMENTS 3,630,602 A * 12/1971 Herbert ............... 351/221
4,065,208 A * 12/1977 Currey ............... 351/219
4,134,647 A    1/1979 Ramos-Caldera
4,598,984 A *  7/1986 Rol ............... 351/219
4,728,183 A    3/1988 Heacock
5,007,729 A    4/1991 Erickson
5,548,352 A *  8/1996 Dewey ............... 351/160 H
5,841,510 A   11/1998 Roggy
6,183,085 B1   2/2001 Roggy

OTHER PUBLICATIONS

Brochure of Ocular Instruments, Inc. entitled "Three Mirror Universal Lens".
Ocular Instruments 2003 Product Catalog.

* cited by examiner

Primary Examiner—Scott J. Sugarman
Assistant Examiner—James R Greece
(74) Attorney, Agent, or Firm—Michael E. Dergosits

(57) ABSTRACT

An improved ophthalmic fundus contact lens to observe and irradiate the interior of the eye. Internally the device consists of a ring of contiguous mirrors (12) with identical angulations arranged around a posterior concave lens (10). The outside surface of the instrument contains a wall (14) of exterior housing. A glass or transparent material (16) covers the anterior opening of the lens. The invention is particularly useful for faster and safer panretinal photocoagulation (PRP).

13 Claims, 2 Drawing Sheets

RING LASER PHOTOCOAGULATION

CROSS-REFERENCE TO RELATED APPLICATIONS

Figure 1:
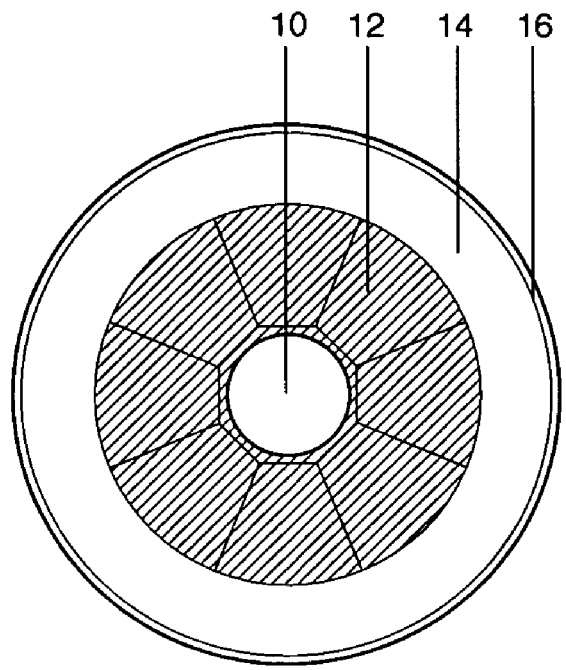

This application claims the benefit of provisional patent application Ser. No. 60/540,810, filed 2004 Jan. 30 by the present inventor.

FEDERALLY SPONSORED RESEARCH

Not Applicable

SEQUENCE LISTING OR PROGRAM

Not Applicable

BACKGROUND OF THE INVENTION—FIELD OF INVENTION

The present invention relates to ophthalmic devices which facilitate diagnosis and delivery of laser energy to the interior of the eye.

BACKGROUND OF THE INVENTION—PRIOR ART

Diagnostic and therapeutic fundoscopic lenses are commonly used for evaluation and treatment of the internal portions of the eye. In order to effectuate treatment for a variety of ocular disorders an ophthalmologist must first see an image of the inner structure of the eye. After an appropriate examination is completed a laser delivery system is used to thermally heat the appropriate anatomical structures within the eye with laser light. The prior technology is well described in this area and often includes a slit lamp biomicroscope used in conjunction with specialized contact lenses. These fundus contact lenses are designed to view different anatomical areas within the eye. The patient's pupil is usually pharmacologically dilated, topical anesthesia is placed on the eye, a coupling agent is placed on the posterior surface of the lens, and the examiner places and hand holds the lens on the surface of the eye. The treating physician must then manipulate the contact lens, the slit lamp illumination beam, and the laser delivery device simultaneously to apply therapy.

A typical example of the prior art in terms of fundus contact lenses would be the three-mirror device. It is currently used by ophthalmologists at the time of this application. Sometimes called the Goldmann contact lens, named after its inventor, and sometimes termed the three-mirror universal contact lens, it consists of a funnel shaped exterior housing. The larger end is covered by a glass or plastic viewing surface while the smaller end of the apparatus has a small hole into which a concave lens is placed. The smaller end fits on the patient's cornea after the suitable application of topical anesthesia and a coupling agent such as methylcellulose. The interior of the assembly consists of three nonmobile mirrors mounted one hundred and twenty degrees apart from each other. The mirrors have different inclinations in space from a vertical plane tangent to the corneal apex. The different angulations of each mirror allow an examiner to view different anatomical areas within the eye. Also, by convention manufacturers configure the mirrors in different shapes so users can readily identify the correct reflecting device for the area of the eye they wish to examine. Although the mirrors are mounted circumferentially around the central posterior concave lens of the apparatus, they do not touch each other and are not contiguous. Furthermore, the heights of each mirror are unequal. As the physician holds the fundus contact lens on the patient's eye he/she manipulates a viewing beam of light from a slit lamp biomicroscope with the other hand. Shining the slit light directly through the central posterior round concave lens allows a view of the internal eye of approximately thirty degrees. Typically, this would include an area comprising the optic nerve, the macula, and out to the edges of the vascular arcades. In addition, by directing the slit beam individually into each of the three mirrors a doctor can view the mid peripheral retina, the peripheral retina, and the anterior segment of the eye.

This lens contains a number of disadvantages. First, although each mirror allows the user to inspect a different anatomical zone within the globe the external lens housing must be manually rotated by the examiner to facilitate examining or treating three hundred sixty degrees within the patient's eye. Second, a subtle tilting of the lens by the treating physician as the device is rotated can cause corneal distortion. Also it can allow loss or dispersion of the coupling agent between the device and the patient's cornea. In some cases the movement allows air bubbles to accumulate under the lens and this adverse event disturbs the examiners view. And, not uncommonly, manual manipulations of the lens can induce some discomfort in the patient's eyelids. Third, this fundus lens must be rotated one hundred eighty degrees opposite the clock hour that is being examined or treated. As a reflecting surface an individual mirror images a view one hundred eighty degrees from the meridian in which it is held on the eye. Thus to see the patient's mid peripheral retina at nine o'clock (horizontal meridian) it is necessary to place the correct mirror within the device at the three o'clock position. Likewise, to treat the twelve o'clock peripheral retina it is necessary to place and use the peripheral mirror at the six o'clock (vertical) meridian. And, to view or treat each clock hour of the patient's eye, presuming the eye is roughly spherical in shape, it is necessary to rotate the fundus contact in a circle so that a given mirror can facilitate three hundred sixty degrees of treatment. And, if another anatomical zone within the eye needs treatment the entire process must be repeated with a different mirror within the device. Fourth, the Goldmann style contact does not facilitate either an automated process for panretinal laser delivery (PRP) or a quicker manual approach with a broad beam laser. Panretinal laser photocoagulation, sometimes termed scatter photocoagulation, is often used to treat proliferative diabetic retinopathy, severe nonproliferative diabetic retinopathy, disc neovascularization due to branch and central retinal vascular occlusions, and neovascular glaucoma. The current state of the art for panretinal photocoagulation (PRP) using a three mirror fundus contact lens requires the treating surgeon to place multiple, Interrupted laser applications one at a time. Typically, the laser shots are aimed and focused using the contact lens in a grid or scatter pattern. The configuration of treatment involves three hundred sixty degrees of a given zone within the eye. Often fifteen hundred to two thousand individual five hundred micron burns are applied to complete a course of therapy. During this process the laser surgeon must simultaneously rotate the contact lens, steady it, focus the slit lamp illumination beam, aim the laser, and trigger the device. Patients are often given therapy in multiple sessions (two to four) lasting twenty minutes each.

It is therefore desirable to provide a device or methodology which would reduce examiner lens manipulations, reduce treatment times, reduce aiming errors, and reduce patient pain during laser procedures. A number of attempts by prior inventors have addressed some of these issues. However, none has achieved the majority of these objectives. U.S. Pat. Nos. 5,841,510 and 6,183,085 to Roggy (1998) (2001) are examples. While the devices claim to minimize external rotations of the contact housing they substitute internal rotation of the instrument mirrors. Holding this contact lens on the eye an examiner is still forced to rotate an annular peripheral member with a forefinger so as to properly place a given mirror in the appropriate position for retinal examination or treatment. In addition, its plurality of mirrors is set to different inclinations relative to the vertical. Thus, since this mirror configuration is identical to the Goldmann lens or the three-mirror universal lens it prevents treating an entire zone of the inner eye without highly coordinated hand movements. In U.S. Pat. No. 4,134,647 to Ramos-Caldera (1979) the device incorporates a stationary parboloidal mirror within the conical housing of a truncate lens. While it purports giving an examining physician a panoramic view of the interior of the eye it forces a user to take extreme care in focusing the slit beam. A subtle difference in aiming the illumination beam within the parabolic surface results in a significant difference in the area of the interior eye that is seen. Furthermore, the mirror curvature that is inherent in this device can induce image distortion. Similarly, incident laser beam distortion is expected. Laser treatment of an entire zone within the eye such as the peripheral retina would tax both time and user coordination.

As a result of some of the aforementioned disadvantages other strategies for fundus lenses have been employed. Although two such attempts U.S. Pat. No. 4,728,183 to Heacock et al. (1988) and U.S. Pat. No. 5,007,729 to Erickson et. al. (1991) made significant advances to image quality and reduced lens manipulations they do not address other matters. Both instruments employ a fixed combination of lenses to produce an aerial image of the retina. However, the first lens with two elements has a field of view that is insufficient for complete panretinal laser treatment. It also suffers from an aerial image that inhibits its usage with some forms of slit lamp biomicroscopes. The second fundus contact by Erickson delivers a wide angle image of the retina with three lens elements. Nonetheless, the observer's view is minified as compared to the three mirror universal lens. Furthermore this contact is not designed for time efficient panretinal photocoagulation nor for potentially automating treatments. An examiner is still forced to focus the lens manually and place laser treatment spots one at a time (i.e. fifteen hundred to two thousand single applications for PRP) within the eye. In addition, this device is not designed for broad beam laser delivery.

BACKGROUND OF THE INVENTION—OBJECTS AND ADVANTAGES

Accordingly, several objects and advantages of my invention are:

a) to provide a faster method of laser treatment for panretinal photocoagulation;

b) to provide an instrument which reduces manual contact lens manipulations by the treating surgeon;

c) to provide a device which reduces user coordination for examination or treatments;

d) to provide a contact lens which reduces patient discomfort with laser procedures;

e) to provide a fundus lens that minimizes aiming errors and increases safety; and f) to provide a method and article of manufacture that facilitates the automated delivery of laser treatments.

Further objects and advantages of my invention will become apparent from a consideration of the drawings and ensuing description.

SUMMARY

The present invention comprises a biomicroscopic fundus contact lens with a body in the shape of a truncated cone. Internally it consists of a plurality of mirrors or prisms mounted in an annular fashion each with identical angulations relative to a vertical line tangential to the corneal surface. The smaller end of the cone contains a round, concave lens for viewing the posterior pole of the eye while the larger end is covered with transparent glass or plastic. In one embodiment the nonmobile mirrors are identically angulated to view the mid peripheral retina and in the second device the mirrors are designed to image the peripheral retina.

DRAWINGS—FIGURES

Figure 2:
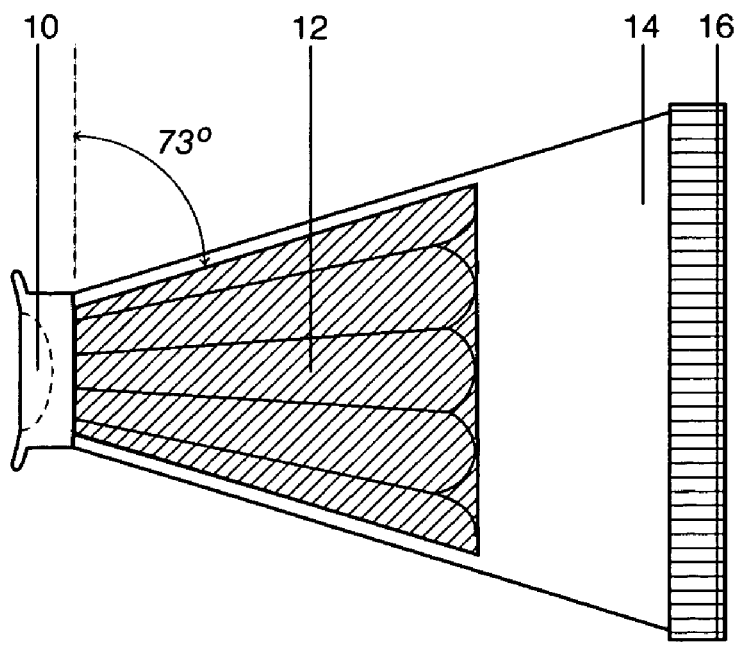
Figure 3:
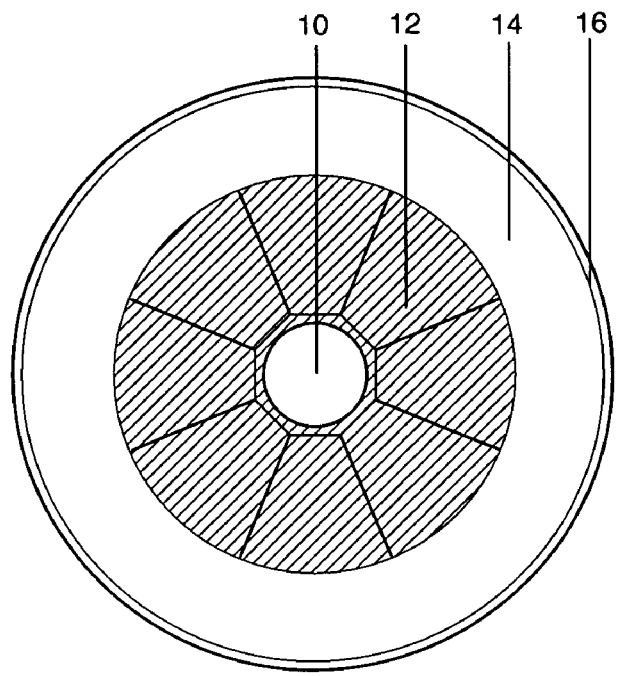

FIG. 1 A view showing the anterior or top of the apparatus as seen by a user performing treatment with the device on the patient's cornea (the individual mirrors within the lens are inclined to seventy three degrees (73)—a circular concave central view lens is located posteriorly-adjacent to the most posterior viewing lens is an annulus of contiguous mirrors with identical angulations circumscribing a circle FIG. 2 A lateral view of the device (with internal mirrors at seventy three degrees (73) showing a rounded external wall, a small concave end for placing on the patient's cornea, and a larger end for hand holding by the user FIG. 3 Top view of the contact lens as shown above but with mirror inclinations at sixty seven degrees (67)

Figure 4:
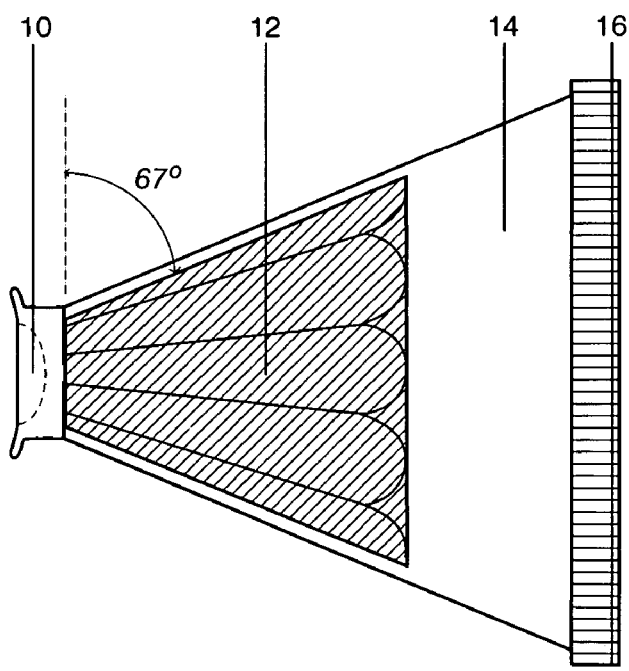

FIG. 4 Side or lateral view of the contact lens shown above and with inner mirror angulations of sixty seven degrees (67)

DRAWINGS—REFERENCE NUMERALS

10 circular opening on the smaller posterior end of the device which contains a concave lens for viewing the posterior pole of the subject's eye

12 plurality of mirrored surfaces arranged circumferentially

14 wall of the external housing of the fundus contact transparent covering of glass or plastic over

16 the anterior surface of the truncated cone

DESCRIPTION—FIGS. 1 AND 2—PREFERRED EMBODIMENT

A preferred embodiment of the fundus contact lens is shown in FIG. 1 and FIG. 2 (side view). The instrument takes the form of a truncated cone. The upper portion of the device has a ridge for handling. On the anterior surface the cone has a transparent covering 16 such as glass or plastic. On the posterior lateral external surface, the wall of the housing 14 is expanded slightly in order to create a flange that will help secure the lens on the patient's eye. The smaller portion of the lens 10 as viewed through the anterior surface of FIG. 1 has a circular opening. Inside the opening a concave lens 10 is placed for viewing the posterior pole of the patient's eye. The posterior surface which contacts the eye is shaped with a radius of curvature such that it approximates the cornea.

Internal to the concave lens 10 a series of contiguous mirrors or prisms 12 are arranged in an annular configuration. Each mirror has identical angulations that will allow a view or treatment of a given zone within the eye. If the mirrors are inclined at seventy three degrees (73) the mid peripheral retina can be imaged. Using laser through these mirrors would result in a treatment pattern than would facilitate a ring or donut shaped area from the vascular arcades to the equator of the eye. With another embodiment of this invention FIG. 3 and FIG. 4, housed in a similar casing, the ring of mirrors is mounted at sixty seven (67) degrees. In that scenario the peripheral retina (from the equator to the ora serrata) can be seen and treated. Neither embodiment (one lens at seventy three (73) degrees of inclination and one with sixty seven (67) degrees of inclination) is intended to view or cause treatment to the anterior segment of the eye. Neither construct has moving parts. Internally each device contains a ring of mirrors and one posterior concave lens. Although in either embodiment the user can view the posterior pole of the eye through the central circular concave lens, it is a goal that this invention be used to effect site specific ocular laser treatment for an entire three hundred sixty (360) degrees. With a broad beam laser this can be done in a single treatment session. Furthermore, with this concept no manual contact lens rotations and no internal manipulations will be required by the treating surgeon. Nothing precludes the device from being used with conventional laser wavelengths (400-700 nm) and conventional beam sizes (500 microns). However, it is anticipated that large or broad beam lasers (3 mm or greater), Including those in the infrared spectrum (810 nm), will be most efficacious in producing a ring of therapy quickly. With this technology multiple, single interrupted small laser spot applications will not have to be done. A relatively large treatment beam will treat an entire annular area within the eye aborting the need for a large number of treatment applications one at a time.

Operation

In order to utilize the device to perform ring panretinal photocoagulation the examiner will first anesthetize the patient's cornea. After a suitable coupling agent (methylcellulose) is applied to the concave end of the apparatus the lens is placed on the patient's cornea. Assuming the physician wishes to first treat the mid peripheral retina the device with mirror inclinations at seventy three (73) will be chosen. Using a biomicroscopic slit lamp beam in conjunction with the posterior concave lens of the device the user can center and focus the macular area through the axial portion of the lens. Then the focus of the mid peripheral retina can be checked through the plurality of internal mirrors within the instrument. Subsequently the laser can be triggered after aiming in the appropriate mirrors. It might be triggered in a manual fashion or by an automated delivery device. By reflection the treatment beam will be delivered as an annulus to the interior of the eye (mid periphery). If the examiner then wishes to treat a broader area internally the lens can be exchanged for the instrument containing mirror inclinations of sixty seven (67) degrees. In this fashion the peripheral retina could also be lasered.

Alternative Embodiments

Without departing from the spirit of my invention, alternatively, one could arrange a series of rectangular, square, or even round mirrors around the concave lens at the posterior portion of the invention. If these individual mirrors all had the same angular inclinations, were the same size, and were in effect contiguous, they would create a ring similar to the preferred embodiment as delineated above. While my primary device as drawn contains eight internal mirrors arranged circumferentially nothing would prevent another embodiment from being constructed with sixteen, thirty two, or any number of mirrors/prisms. Furthermore, nothing prevents the internal mirrors with the different angulations from being placed in one device instead of two. Also, while this invention promulgates the potential concept of minimal shot ring laser panretinal photocoagulation (PRP) this methodology might be achieved in other forms. In one instance a selective coating to block laser reflection might be applied to some of the current wide field fundus contact lenses on the market. The net effect might be to create an annular beam to effectuate treatment. This creation of a ring pattern to the laser instillation could also be accomplished mechanically at the laser end by beam splitters. Similarly a modification of the laser aperture might create a donut configuration to the treatment beam.

Advantages

From the description above, a number of advantages of my ring fundus contact lens become evident. First, these devices can facilitate a faster way to effectuate laser treatment. Without having to rotate a mirror manually to deliver the beam the speed of treatment can be quicker. In addition, the lack of moving parts internally prevents extra manipulations by the examiner. If used in conjunction with a broad beam laser (large spot size) a complete panretinal photocoagulation might be reduced to eight or sixteen shots. This is in marked contrast to the fifteen hundred to two thousand applications that are currently used. Furthermore, if the laser delivery process is subsequently automated, a complete therapy might be reduced to seconds. This stands in marked contrast to the two or three twenty minute treatment sessions in vogue today. Even when the laser delivery is not through the conventional slit lamp, such as the indirect ophthalmoscope, multiple treatment spots and multiple sessions are still the standard for panretinal photocoagulation. Second, the invention reduces hand held external lens or internal mirror adjustments. Third, with the mirrors fixed in a ring configuration to image or treat a specific zone of the retina user coordination is minimized. Fourth, the lens facilitates greater patient comfort because of less lens movement under the lids. Fifth, these lenses reduce surgeon aiming errors and enhance safety because laser delivery is not as dependent on subtle changes in focus or target location as in other models. Finally, this device stands as a bridge to facilitate automating the process of retinal photocoagulation.

Conclusions, Ramifications, and Scope

Thus the reader can see that this invention can provide a simpler, faster, and safer method for performing retinal laser photocoagulation. This is accomplished by the ring configuration of mirrors or prisms which facilitates broad beam laser treatment, reduced treatment times, less examiner aiming errors, fewer lens manipulations, increased patient safety, and a means to automate panretinal laser photocoagulation.

While my above description contains many specificities, these should not be construed as limitations on the scope of the invention. Rather, they should be considered as an exemplification of the preferred embodiment. Many other variations are possible. For example, the external body of my ring contact lens does not have to be a truncated cone. It might be cylindrical in shape. In addition, the number of internal mirrors arranged in a circular configuration does not have to be eight as drawn above. There could be six, sixteen, thirty two, or any other number. And, the mirror shapes are not restricted to trapezoidal. They might be rectangular, square, or even round in shape. Finally, the identical angulations of the mirrors do not have be specifically seventy three (73) and sixty seven (67) degrees. A spectrum of inclinations exist which might serve to image the mid peripheral and the peripheral retina.

Thus the scope of the invention should be determined by the appended claims and their legal equivalents.

I claim:

1. An ophthalmic fundus contact lens comprising:
   (a) a casing with an anterior surface and with a posterior surface, the posterior surface adapted to be placed in contact with the surface of an eye,
   (b) within the casing between posterior and anterior surfaces, a plurality of mirrors or prisms mounted in a contiguous and annular fashion with identical inclinations relative to a vertical line tangential to the eye corneal apex for viewing the eye retina/choroids within said casing, and,
   (c) a lens proximate the posterior surface of the casing to image the posterior pole of the eye.

2. The fundus contact lens of claim 1 wherein said plurality of mirrors or prisms is serially connected in a circular array.

3. The fundus contact lens of claim 1 wherein said plurality of mirrors or prisms are touching each other and between six and twelve in number.

4. The fundus contact lens of claim 1 wherein said casing is cylindrical or conical in shape.

5. The fundus contact lens of claim 1 wherein one end is designed to fit on the human cornea.

6. The fundus contact lens of claim 1 wherein the casing is fabricated from an acrylic polymer.

7. The fundus contact lens of claim 1 wherein the anterior surface is composed of a transparent material.

8. The fundus contact lens of claim 1 wherein a said lens to image the posterior pole of the eye is concave.

9. A method of heating the posterior segment of a patient's eye by laser energy for panretinal coagulation comprising the steps of:
   (a) anesthetizing the patient's cornea;
   (b) providing an ophthalmic fundus contact lens having (i) a casing with an anterior surface and with a posterior surface, the posterior surface adapted to be placed in contact with the surface of the eye; (ii) within the casing between posterior and anterior surfaces, a plurality of mirrors or prisms mounted in a contiguos and annular fashion with identical inclinations relative to a vertical line targeted to the eye corneal apex for viewing the eye retina/choroids; and (iii) a lens proximate the posterior surface of the casing;
   (c) applying a coupling agent to the posterior surface of the ophthalmic contact lens;
   (d) placing the ophtahnic fundus contact lens on the patient's cornea; and
   (e) delivering a laser beam to the ring of mirrors arranged circumferentially within the fundus contact lens, whereby retinal treatment occurs when the laser beam reflects off of the mirrors or prisms into the interior of the patient's eye.

10. The method of claim 9 wherein said casing is fabricated from a light weight polymer.

11. The method of claim 9 wherein said casing is conoid in shape.

12. The method of claim 9 wherein said mirrors or prisms have an antireflective coating.

13. The method of claim 9 wherein mirror or prism inclinations are devised to treat the patient's mid and peripheral retina.

\* \* \* \* \*